(12) United States Patent
Li et al.

(10) Patent No.: US 8,391,943 B2
(45) Date of Patent: Mar. 5, 2013

(54) MULTI-WAVELENGTH PHOTON DENSITY WAVE SYSTEM USING AN OPTICAL SWITCH

(75) Inventors: Youzhi Li, Longmont, CO (US); Andy S. Lin, Boulder, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 352 days.

(21) Appl. No.: 12/751,264

(22) Filed: Mar. 31, 2010

(65) Prior Publication Data

US 2011/0245636 A1 Oct. 6, 2011

(51) Int. Cl.
*A61B 5/00* (2006.01)
*A61B 6/00* (2006.01)

(52) U.S. Cl. .......................... 600/323; 600/476

(58) Field of Classification Search .................. 600/323, 600/324, 326, 476
See application file for complete search history.

(56) References Cited

U.S. PATENT DOCUMENTS

| | | |
|---|---|---|
| 3,638,640 A | 2/1972 | Shaw |
| 4,223,680 A | 9/1980 | Jobsis |
| 4,936,679 A | 6/1990 | Mersch |
| 4,971,062 A | 11/1990 | Hasebe et al. |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,088,493 A | 2/1992 | Giannini et al. |
| 5,119,815 A | 6/1992 | Chance |
| 5,253,646 A | 10/1993 | Delpy et al. |
| 5,275,159 A | 1/1994 | Griebel |
| 5,353,799 A | 10/1994 | Chance |
| 5,416,582 A | 5/1995 | Knutson et al. |
| 5,424,843 A | 6/1995 | Tromberg et al. |
| 5,441,054 A | 8/1995 | Tsuchiya |

(Continued)

FOREIGN PATENT DOCUMENTS

| | | |
|---|---|---|
| EP | 497021 | 5/1992 |
| EP | 0580414 A2 | 1/1994 |

(Continued)

OTHER PUBLICATIONS

Ntziachristos, et al.; "Oximetry based on diffuse photon density wave differentials;" Medical Physics, AIP, vol. 27, No. 2, Feb. 1, 2000; pp. 410-421.

(Continued)

*Primary Examiner* — W.B. Perkey
(74) *Attorney, Agent, or Firm* — Fletcher Yoder

(57) ABSTRACT

Multi-wavelength photon density wave (PDW) medical systems, methods, and devices are provided. In one embodiment, a multi-wavelength system may include a sensor, a sensor cable, and a patient monitor. The sensor may have an emitter and a detector configured to pass a multi-wavelength PDW input signal into a patient and receive a resulting multi-wavelength PDW output signal. The sensor cable may couple to the sensor and include two optical cables for transmitting and receiving the multi-wavelength PDW signals. The patient monitor may couple to the sensor cable and generate several single-wavelength PDW input signals by modulating a plurality of light sources. The monitor may include an optical switch configured to time-division multiplex the several single-wavelength PDW wave input signals by selecting one of the single-wavelength PDW signals at one time to produce a multi-wavelength PDW signal which is output from the monitor to the sensor via the sensor cable.

17 Claims, 8 Drawing Sheets

U.S. PATENT DOCUMENTS

| | | | |
|---|---|---|---|
| 5,477,051 A | 12/1995 | Tsuchiya | |
| 5,483,646 A | 1/1996 | Uchikoga | |
| 5,492,118 A | 2/1996 | Gratton et al. | |
| 5,497,769 A | 3/1996 | Gratton et al. | |
| 5,730,124 A | 3/1998 | Yamauchi | |
| 5,772,587 A | 6/1998 | Gratton et al. | |
| 5,779,631 A | 7/1998 | Chance | |
| 5,800,348 A | 9/1998 | Kaestle | |
| 5,813,988 A | 9/1998 | Alfano et al. | |
| 5,818,583 A | 10/1998 | Sevick-Muraca et al. | |
| 5,830,139 A | 11/1998 | Abreu | |
| 5,831,598 A | 11/1998 | Kauffert et al. | |
| 5,859,713 A | 1/1999 | Khoury et al. | |
| 5,871,442 A | 2/1999 | Madarasz et al. | |
| 5,873,821 A | 2/1999 | Chance et al. | |
| 6,009,340 A * | 12/1999 | Hsia | 600/407 |
| 6,064,917 A | 5/2000 | Matson | |
| 6,078,833 A * | 6/2000 | Hueber | 600/476 |
| 6,081,742 A | 6/2000 | Amano et al. | |
| 6,120,460 A | 9/2000 | Abreu | |
| 6,134,460 A | 10/2000 | Chance | |
| 6,192,260 B1 | 2/2001 | Chance | |
| 6,192,261 B1 | 2/2001 | Gratton et al. | |
| 6,246,892 B1 | 6/2001 | Chance | |
| 6,272,367 B1 | 8/2001 | Chance | |
| 6,285,895 B1 | 9/2001 | Ristolainen et al. | |
| 6,309,352 B1 | 10/2001 | Oraevsky et al. | |
| 6,312,393 B1 | 11/2001 | Abreu | |
| 6,335,792 B1 | 1/2002 | Tsuchiya | |
| 6,353,750 B1 | 3/2002 | Kimura et al. | |
| 6,415,236 B2 | 7/2002 | Kobayashi et al. | |
| 6,419,671 B1 | 7/2002 | Lemberg | |
| 6,453,183 B1 | 9/2002 | Walker | |
| 6,456,862 B2 | 9/2002 | Benni | |
| 6,461,305 B1 | 10/2002 | Schnall | |
| 6,487,439 B1 | 11/2002 | Skladnev et al. | |
| 6,493,565 B1 | 12/2002 | Chance et al. | |
| 6,542,772 B1 | 4/2003 | Chance | |
| 6,544,193 B2 | 4/2003 | Abreu | |
| 6,549,284 B1 | 4/2003 | Boas et al. | |
| 6,549,795 B1 | 4/2003 | Chance | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,618,042 B1 | 9/2003 | Powell | |
| 6,618,614 B1 | 9/2003 | Chance | |
| 6,622,095 B2 * | 9/2003 | Kobayashi et al. | 702/31 |
| 6,662,030 B2 | 12/2003 | Khalil et al. | |
| 6,671,528 B2 | 12/2003 | Steuer et al. | |
| 6,675,029 B2 | 1/2004 | Monfre et al. | |
| 6,687,519 B2 | 2/2004 | Steuer et al. | |
| 6,690,958 B1 | 2/2004 | Walker et al. | |
| 6,704,110 B2 | 3/2004 | Tsuchiya | |
| 6,711,426 B2 | 3/2004 | Benaron et al. | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,802,812 B1 | 10/2004 | Walker et al. | |
| 6,850,053 B2 | 2/2005 | Daalmans et al. | |
| 6,859,658 B1 | 2/2005 | Krug | |
| 6,873,865 B2 | 3/2005 | Steuer et al. | |
| 6,882,874 B2 | 4/2005 | Huiku | |
| 6,898,451 B2 | 5/2005 | Wuori | |
| 6,944,322 B2 | 9/2005 | Johnson et al. | |
| 6,947,781 B2 | 9/2005 | Asada et al. | |
| 6,949,081 B1 | 9/2005 | Chance | |
| 6,957,094 B2 | 10/2005 | Chance et al. | |
| 7,006,676 B1 | 2/2006 | Zeylikovich et al. | |
| 7,006,856 B2 | 2/2006 | Baker et al. | |
| 7,010,341 B2 | 3/2006 | Chance | |
| 7,035,697 B1 | 4/2006 | Brown | |
| 7,041,063 B2 | 5/2006 | Abreu | |
| 7,043,289 B2 | 5/2006 | Fine et al. | |
| 7,065,392 B2 | 6/2006 | Kato | |
| 7,072,701 B2 | 7/2006 | Chen et al. | |
| 7,095,491 B2 | 8/2006 | Forstner et al. | |
| 7,139,603 B2 | 11/2006 | Chance | |
| 7,164,938 B2 | 1/2007 | Geddes et al. | |
| 7,184,148 B2 | 2/2007 | Alphonse | |
| 7,187,441 B1 | 3/2007 | Sevick-Muraca et al. | |
| 7,197,355 B2 | 3/2007 | Nelson | |
| 7,236,811 B2 | 6/2007 | Schmitt | |
| 7,239,902 B2 | 7/2007 | Schmitt et al. | |
| 7,251,518 B2 | 7/2007 | Herrmann | |
| 7,268,873 B2 | 9/2007 | Sevick-Muraca et al. | |
| 7,272,426 B2 | 9/2007 | Schmid | |
| 7,277,741 B2 | 10/2007 | Debreczeny et al. | |
| 7,283,242 B2 | 10/2007 | Thornton | |
| 7,327,463 B2 | 2/2008 | Alphonse | |
| 7,330,746 B2 | 2/2008 | Demuth et al. | |
| 7,355,688 B2 | 4/2008 | Lash et al. | |
| 7,469,158 B2 | 12/2008 | Cutler et al. | |
| 7,483,731 B2 | 1/2009 | Hoarau et al. | |
| 7,500,953 B2 | 3/2009 | Oraevsky et al. | |
| 7,525,647 B2 | 4/2009 | Lash et al. | |
| 7,538,865 B2 | 5/2009 | Lash et al. | |
| 7,551,950 B2 | 6/2009 | Cheng | |
| 7,621,877 B2 | 11/2009 | Schnall | |
| 7,623,285 B2 | 11/2009 | Gross | |
| 7,689,259 B2 | 3/2010 | Mannheimer et al. | |
| 7,753,902 B1 * | 7/2010 | Mansour et al. | 604/541 |
| 2002/0042558 A1 | 4/2002 | Mendelson | |
| 2002/0156354 A1 | 10/2002 | Larson | |
| 2002/0198443 A1 | 12/2002 | Ting | |
| 2003/0023140 A1 | 1/2003 | Chance | |
| 2005/0059870 A1 | 3/2005 | Aceti | |
| 2005/0113651 A1 | 5/2005 | Wood et al. | |
| 2005/0113656 A1 | 5/2005 | Chance | |
| 2005/0192488 A1 | 9/2005 | Bryenton et al. | |
| 2005/0228248 A1 | 10/2005 | Dietiker | |
| 2005/0250998 A1 | 11/2005 | Huiku | |
| 2006/0020181 A1 | 1/2006 | Schmitt | |
| 2006/0122475 A1 | 6/2006 | Balberg et al. | |
| 2006/0135860 A1 | 6/2006 | Baker et al. | |
| 2006/0189861 A1 | 8/2006 | Chen et al. | |
| 2006/0247501 A1 | 11/2006 | Ali | |
| 2006/0247506 A1 | 11/2006 | Balberg et al. | |
| 2007/0093702 A1 | 4/2007 | Yu et al. | |
| 2007/0129613 A1 | 6/2007 | Rochester et al. | |
| 2008/0139908 A1 | 6/2008 | Kurth | |
| 2008/0312533 A1 | 12/2008 | Balberg et al. | |
| 2010/0016732 A1 | 1/2010 | Wells et al. | |
| 2011/0118574 A1 * | 5/2011 | Chang et al. | 600/324 |

FOREIGN PATENT DOCUMENTS

| | | |
|---|---|---|
| EP | 832599 | 1/1998 |
| EP | 0945100 A1 | 9/1999 |
| WO | WO9313706 | 7/1993 |
| WO | WO9727801 | 8/1997 |
| WO | 00/25112 A1 | 5/2000 |
| WO | WO0140776 | 6/2001 |
| WO | WO03077750 | 9/2003 |
| WO | WO2004010844 | 2/2004 |
| WO | WO2005025399 | 3/2005 |
| WO | WO2005064314 | 7/2005 |
| WO | WO2006097910 | 9/2006 |
| WO | WO2006124455 | 11/2006 |
| WO | WO2006124696 | 11/2006 |
| WO | WO2007048039 | 4/2007 |
| WO | 2010/039418 A2 | 4/2010 |
| WO | 2011/034699 A2 | 3/2011 |
| WO | 2011/034700 A2 | 3/2011 |
| WO | 2011/041071 A2 | 4/2011 |

OTHER PUBLICATIONS

Ulas, et al.; "Noninvasive diffuse optical measurement of blood flow and blood oxygenation for monitoring radiation therapy in patients with head and neck tumors: a pilot study;" Journal of Biomedical Optics, vol. 11, No. 6; Jan. 1, 2006, p. 064021.

International Search Report and Written Opinion for PCT Application No. PCT/US2011/028437 dated Jul. 14, 2011, 15 pgs.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Aoyagi, T., et al.; "Analysis of Motion Artifacts in Pulse Oximetry," *Japanese Society ME*, vol. 42, p. 20 (1993) (Article in Japanese—contains English summary of article).

Barreto, Armando B., et al.; "Adaptive LMS Delay Measurement in dual Blood Volume Pulse Signals for Non-Invasive Monitoring," *IEEE*, pp. 117-120 (1997).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie.*

Goldman, Julian M.; "Masimo Signal Extraction Pulse Oximetry," *Journal of Clinical Monitoring and Computing*, vol. 16, pp. 475-483 (2000).

Hamilton, Patrick S., et al.; "Effect of Adaptive Motion-Artifact Reduction on QRS Detection," *Biomedical Instrumentation & Technology*, pp. 197-202 (undated).

Huang, J., et al.; "Low Power Motion Tolerant Pulse Oximetry," *Abstracts*, A7, p. S103. (undated).

Johansson, A.; "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform," pp. II-310-II-311 (undated).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Lutter, N., et al.; "Comparison of Different Evaluation Methods for a Multi-wavelength Pulse Oximeter," *Biomedizinische Technik*, vol. 43, (1998).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Neumann, et al.; "Fourier Artifact suppression Technology Provides Reliable $SpO_2$," *Abstracts*, A11, p. S105. (undated).

Odagiri, Y.; "Pulse Wave Measuring Device," *Micromechatronics*, vol. 42, No. 3, pp. 6-11 (undated) (Article in Japanese—contains English summary of article).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sept.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

\* cited by examiner

MULTI-WAVELENGTH PHOTON DENSITY WAVE SYSTEM USING AN OPTICAL SWITCH

BACKGROUND

The present disclosure relates generally to non-invasive measurement of physiological parameters and, more particularly, to multi-wavelength photon density wave measurements of physiological parameters.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the absorption and scattering of the light through the tissue. Typical pulse oximetry technology may employ two light emitting diodes (LEDs) and a single optical detector to measure pulse and oxygen saturation of a given tissue bed.

A typical signal resulting from the sensed light may be referred to as a plethysmograph waveform. The plethysmograph waveform is largely based on absorption of emitted light by specific types of blood constituents and may be used with various algorithms to estimate a relative amount of blood constituent in the tissue. For example, the plethysmograph waveform may provide a ratio of oxygenated hemoglobin to total hemoglobin in the volume being monitored. The amount of arterial blood in the tissue is generally time-varying during a cardiac cycle, which is reflected in the plethysmographic waveform.

The accuracy of blood flow characteristic estimation via pulse oximetry may depend on a number of factors. For example, variations in light absorption characteristics can affect accuracy, and such variations may depend on where the sensor is located and/or the physiology of the patient being monitored. Additionally, various types of noise and interference can create inaccuracies. For example, electrical noise, physiological noise, and other interference can contribute to inaccurate blood flow characteristic estimates.

BRIEF DESCRIPTION OF THE DRAWINGS

Advantages of the presently disclosed subject matter may become apparent upon reading the following detailed description and upon reference to the drawings in which.

DETAILED DESCRIPTION

Figure 1:
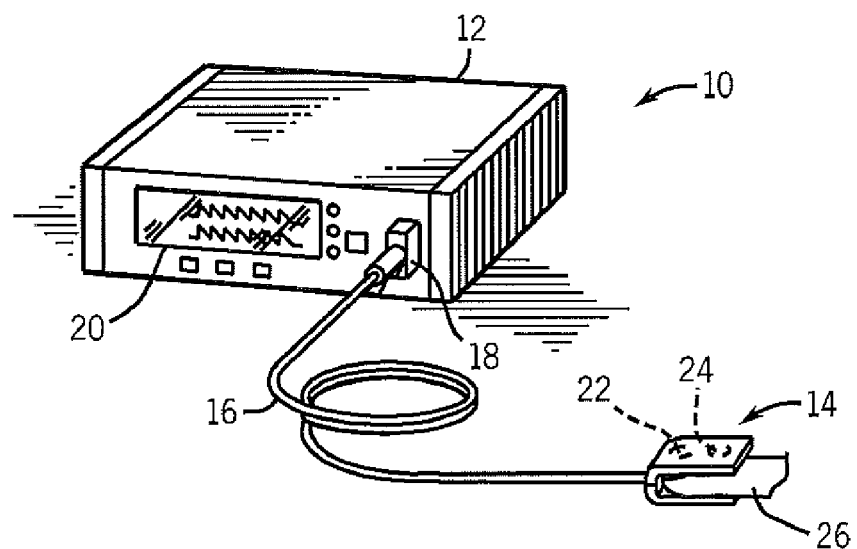
FIG. 1 is a perspective view of a pulse oximeter system in accordance with an embodiment.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiological parameters corresponding to blood flow in a patient. Specifically, light may be emitted into a patient and photoelectrically detected after having propagated through (e.g., transmitted through, scattered by, and/or reflected by) pulsatile tissue of a patient. The propagation of light through pulsatile tissue may by affected by the composition of the tissue, which may vary as blood enters and exits the pulsatile tissue. Rather than emitting a light signal modulated at a rate that is effectively DC through the pulsatile patient tissue, present embodiments involve emitting a light modulated at frequencies sufficient to produce waves of photons known as photon density waves. A photon density wave may refer to light that is modulated at frequencies of approximately 50 MHz-3 GHz. Photon density waves may be resolvable in pulsatile tissue because the photon density waves may have a wavelength that is shorter than a mean absorption distance in pulsatile tissue.

A photon density wave ("PDW") signal that has propagated through the pulsatile tissue of the patient may be detected and analyzed to obtain absorption and/or scattering properties of the pulsatile patient tissue. Certain changes between the PDW signal emitted into the tissue (i.e., the input signal) and the PDW signal detected after propagating through the tissue (i.e., an output signal) may be indicative of tissue conditions. In particular, a change in amplitude between the output signal and the input signal may correspond to absorptive components in the pulsatile tissue. A change in phase between the output signal and the input signal may correspond to scattering components in the pulsatile tissue.

Changes in amplitude of the PDW signals may correspond to the amount of absorptive components in the pulsatile patient tissue, as certain components of the tissue may absorb different wavelengths of light, such as red or infrared light, in different amounts. By analyzing decreases in amplitudes between the output signal and the input signal, a ratio of different types of particles in the pulsatile patient tissue, such as oxygenated and deoxygenated hemoglobin, may be estimated.

Changes in phase of the PDW signals may correspond to the total number of scattering particles in the area of measurement of the patient tissue. More specifically, the phase change between the output signal and the input signal may correspond to the total number of particles (e.g., total hemoglobin) which scatter the PDW signal, and not merely a ratio of particles (e.g., oxygenated and total hemoglobin). Further, variations in the phase change may also be measured to provide information associated with variations of total particles in the patient tissue. With measurements of absorption and scattering by components of the patient tissue, physiological parameters such as $SpO_2$, regional oxygen saturation, total hemoglobin, perfusion, and many others may be monitored.

Thus, PDW signals may be used in the present embodiments to provide physiological information based on the amplitude and phase change of the detected output signal. It is now recognized that using multiple PDW signals having different wavelengths may provide even more physiological information, as patient tissue may have different components of interest (e.g., various types of cells or structures), which may each have different absorption and scattering coefficients. To emit multiple wavelengths of PDW signals to the patient tissue, multiple optical fibers may be used to transmit the generated PDW signals from the monitor to the sensor and into the patient tissue. Likewise, multiple detectors may be used to detect the PDW signals that have propagated through the patient tissue. However, such a configuration may increase system complexity and cost.

In accordance with the present techniques, multiple PDW signals of various wavelengths of light may be time-division multiplexed using an optical switch, such that one wavelength of light is transmitted through a single emission optical cable at any one instant. Thus, the single emission optical cable may transmit to a sensor a multi-wavelength PDW signal which includes multiple single-wavelength PDW signal components transmitted in series over time. Such a multi-wavelength PDW signal (i.e., the input signal), emitted from the sensor into pulsatile patient tissue, may be received by a detector in the sensor after propagating (e.g., reflecting, scattering, and/or passing) through the tissue. Thereafter, a single optical cable may carry the received signal (i.e., the output signal) to the patient monitor. Since the multi-wavelength PDW input signal is time-division multiplexed, only one wavelength of the output signal is received at one time. Thus, a single detector may photoelectrically detect and digitize the output signal. The detected and digitized output signal may be demultiplexed into its component single-wavelength PDW signals and processed to determine various physiological parameters based on comparisons with the multi-wavelength PDW input signal.

With the foregoing in mind, FIG. 1 illustrates a perspective view of a PDW pulse oximetry system 10, which may include a patient monitor 12 and a pulse oximeter sensor 14. A sensor cable 16 may connect the patient monitor 12 to the sensor 14, and may include two fiber optic cables. One of the fiber optic cables within the sensor cable 16 may transmit a multi-wavelength PDW input signal from the patient monitor 12 to be emitted into the patient tissue 26 by an emitter 22 on the sensor 14. The multi-wavelength PDW input signal may propagate through the patient tissue 26 and be received as an output signal by a detector 24 on the sensor 14. Another of the fiber optic cables may transmit the output signal from the sensor 14 to the patient monitor 12. The cable 16 may couple to the monitor 12 via an optical connection 18. Based on signals received from the sensor 14, the patient monitor 12 may determine certain physiological parameters that may appear on a display 20. Such parameters may include, for example, a plethysmogram or numerical representations of patient blood flow (e.g., partial oxygen saturation or a measurement of total hemoglobin).

Figure 2:
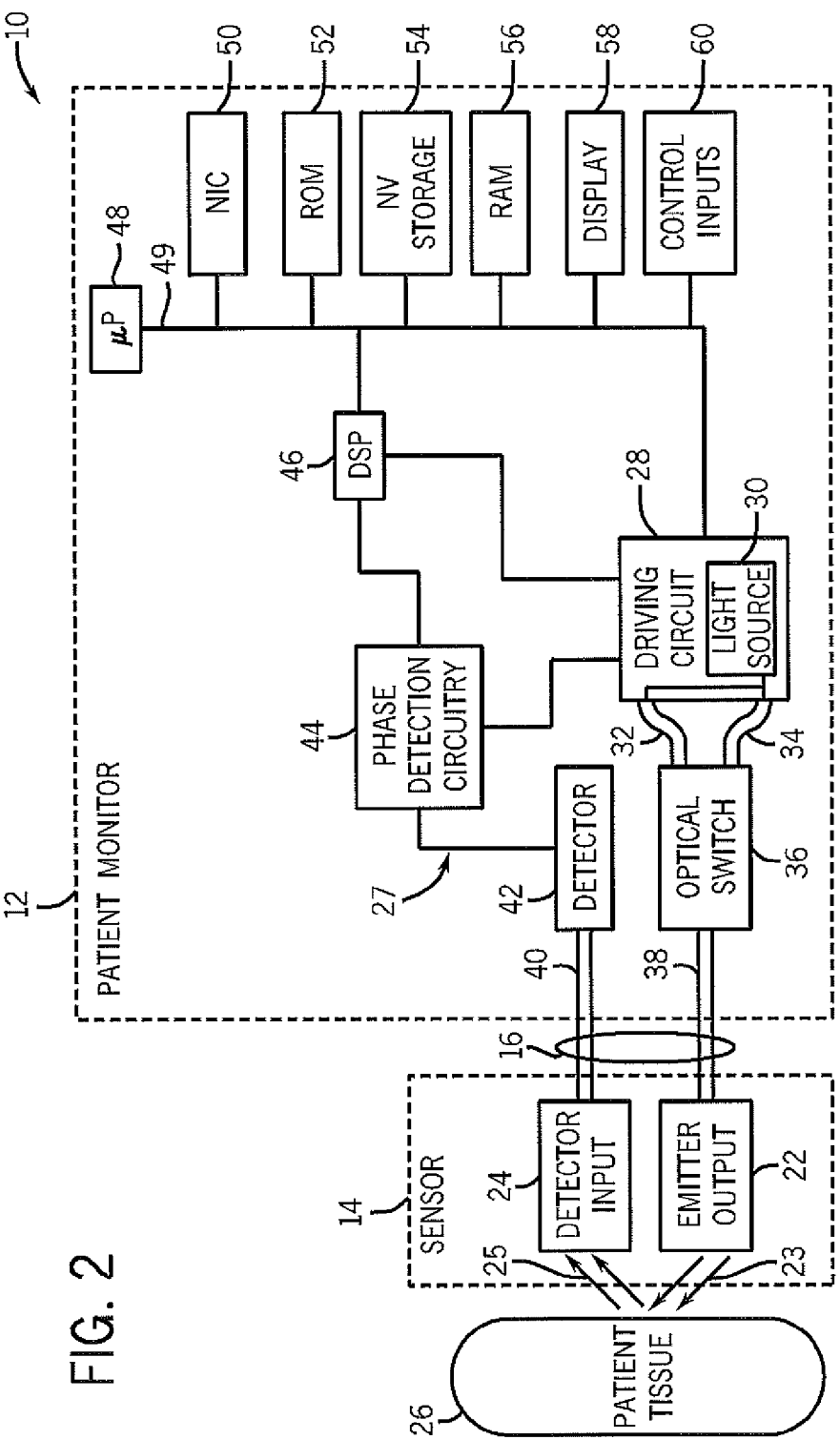
FIG. 2 is a block diagram of the pulse oximeter system of FIG. 1, in accordance with an embodiment.

FIG. 2 represents a block diagram of the system 10 of FIG. 1. Specifically, FIG. 2 more clearly illustrates that the patient monitor 12 may generate several single-wavelength PDW signals which may be transmitted via the sensor cable 16 to the sensor 14 at alternating periods of time (e.g., approximately 1-10 ms, and 4.5 ms in one embodiment) using a driving circuit 28. The driving circuit 28 may include multiple light sources 30 (e.g., laser diodes) which may each emit a wavelength of light. Such wavelengths may include red wavelengths of between approximately 600-700 nm (e.g., 660 nm), infrared wavelengths of between approximately 800-1000 nm (e.g., 900 nm), and/or any other wavelength which may be emitted into and detected from the patient tissue 26 to provide physiological information. For example, in one embodiment, the light sources 30 of the driving circuit 28 may also emit a far red wavelength of between approximately 690-770 nm (e.g., 730 nm). Other wavelengths that may be emitted by the multiple light sources 30 of the driving circuit 28 may include, for example, wavelengths of between approximately 500-600 nm and/or 1000-1100 nm.

The driving circuit 28 may modulate light emitted from the light sources 30 at a modulation frequency between approximately 50 MHz to 3 GHz, which may produce resolvable photon density waves in pulsatile tissue. In some embodiments, the driving circuit 28 may sweep the modulation frequency of one or more of the light sources in a range from 50 MHz to 2.4 GHz. Some embodiments of the patient monitor 12 may be configured to modulate light between 100 MHz and 1 GHz or to sweep a range from 100 MHz to 1 GHz. The driving circuit 28 may, in certain embodiments, modulate the light sources primarily at a frequency of approximately 500 MHz. Examples of PDW signals that may be generated by the driving circuit 28 of the patient monitor 12 may be illustrated below with reference to FIGS. 3 and 4. The modulation frequency used to modulate each wavelength of light may vary, and light emitted from one of the light sources 30 may be modulated at a higher or lower modulation frequency than light emitted from another of the light sources 30. The driving circuit 28 may represent one or more components of commonly available drive circuits (e.g., DVD R/W driver circuits) for modulation. Examples of such devices may include the LMH6525 device available from National Semiconductor Inc. In FIG. 2, the driving circuit 28 is illustrated as being configured to generate two single-wavelength photon density wave signals of different wavelengths respectively through optical cables 32 and 34. However, it should be appreciated that the driving circuit 28 may be designed to generate any suitable number of single-wavelength PDW signals.

An optical switch 36 may switch between the two optical cables 32 and 34, selecting one of the two modulated single-wavelength PDW signals, such that a multi-wavelength PDW signal is produced with multiple single-wavelength PDW signal portions in series. The switching of the optical switch 36 may time-division multiplex the single-wavelength PDW signals from the optical cables 32 and 34 to form the multi-wavelength PDW signal. Each of the single-wavelength PDW signals is alternatingly the sole wavelength active in the multi-wavelength PDW signal for brief periods of time (e.g., on the order of several ms). In other words, the multi-wavelength PDW signal includes several time-multiplexed components of single-wavelength PDW signals. Generally, periods of time that each single wavelength PDW signal is active may be brief enough to enable each of the single-wavelength PDW signals to pass through the pulsatile tissue with substantially no perceptible change in the pulsatile tissue of the patient occurring between the start of the first single-wavelength PDW signal and the end of the last single-wavelength PDW signal in the multi-wavelength PDW signal. Furthermore, the periods may be brief enough such that a pulse through the pulsatile tissue may be adequately sampled by each of the single-wavelength PDW signals. An example of a multi-wavelength PDW signal composed of time-multiplexed single-wavelength PDW signals is illustrated below with reference to FIG. 5.

The optical switch 36 may be any circuit element capable of selecting one single-wavelength PDW signal generated by the driving circuit 28 at one time. In some embodiments, the optical switch 36 may switch between the two optical cables 32 and 34 mechanically. For example, the optical switch 36 may alternate between providing an optical route for each of the two optical cables 32 and 34 to the emitter output 22. Further, the optical switch 36 may be capable of steering light by switching or altering the wavelengths of a signal provided by either of the two optical cables 32 and 34. In some embodiments, the optical switch 36 may enable the constant operation of multiple light sources 30 in the driving circuit 28, which may decrease the complexity of the driving circuit 28 and improve the stability of the light sources 30 while still producing a multi-wavelength PDW signal.

The multi-wavelength PDW signal resulting from the switching of the optical switch 36 may be transmitted through a single optical cable 38 to be emitted into the patient tissue 26 via the emitter output 22 of the sensor 14. An input signal 23 (i.e., multi-wavelength PDW signal emitted by the emitter output 22 into the pulsatile patient tissue 26) may then propagate through the pulsatile tissue 26. The detector input 24 may receive a resulting output signal 25 (i.e., portions of the input signal 23 that have propagated through the patient tissue 26) and transmit the output signal 25 to the patient monitor 12 over an optical cable 40. In one or more embodiments, the optical cable 40 may be a second of only two optical cables of the sensor cable 16.

Because the multi-wavelength PDW signal represents a time-division multiplexed combination of the several single-wavelength PDW signals, only one of the single-wavelength PDW signals generally may pass through the patient tissue 26 at any given time. As such, the output signal 25 may generally be photoelectrically detected in a single photodetector 42, which may receive and convert the optical output signal 25 to an electrical signal referred to as a digitized output signal 27.

The digitized output signal 27 from the detector 42 may enter phase detection circuitry 44, and the output of the phase detection circuitry 44 may be entered into a processor, such as a digital signal processor (DSP) 46, to be analyzed for phase and amplitude changes. The driving circuit 28 may provide the phase detection circuitry 44 and the DSP 46 with information regarding the input signal 23 generated by the driving circuit 28. The information may include reference signals and time-division information relating to the input signal 23. The reference signals may be digital representations of the input signal 23, and may enable the phase detection circuitry 44 and the DSP 46 to analyze amplitude and phase changes between the output signal 25 and corresponding portions of the input signal 23. The time-division information may indicate which single-wavelength PDW signal is currently being received and may enable the phase detection circuitry 44 and the DSP 46 to distinguish between the multiple single-wavelength PDW signals of the multi-wavelength PDW signal. Thus, the DSP 46 may use the time-division information to demultiplex the multi-wavelength PDW signal into its component single-wavelength PDW signals.

By analyzing changes in amplitude and phase between the output signal 25 and the input signal 23, absorption and scattering properties of the patient tissue 26 for that wavelength of light may be determined. To determine amplitude and phase changes corresponding to absorption and scattering in the patient tissue 26, the phase detection circuitry 44 may obtain the output signal 25 (which may be digitized by the detector 42), time-division information, clock signals, and/or reference signals relating to the corresponding original input signal 23. By comparing amplitude changes between the digitized output signal 25 and the input signal 23 (or a digital reference signal corresponding to the input signal 23), absorption properties of the patient tissue 26 for each wavelength of light may be determined. Further, the phase detection circuitry 44 may detect phase changes between the output signal 25 and the input signal 23 to determine scattering properties in the patient tissue 26. In certain embodiments, the phase detection circuitry 44 and the driving circuit 28 may be individual components of a single semiconductor device, such as a DVD R/W driver circuit.

The DSP 46 may receive the output from the phase detection circuitry 44 and time-division information and/or reference signal information from the driver circuit 28. Using the absorption and scattering information associated with the amplitude changes and phase changes between the input signal 23 and the output signal 25, the DSP 46 may determine a variety of properties based on algorithms stored in memory on the DSP 46 or received from external sources, such as a microprocessor 48 or other devices via a bus 49. One example of such an algorithm may be described below with reference to FIG. 8.

In general, the DSP 46 may ascertain certain properties of the patient tissue 26 based on the relationships described below. For a modulation frequency where the product of the frequency and the mean time between absorption events is much larger than 1, the change in phase $\Delta\phi$ between two points located a distance r from each other on a tissue bed may be given by the following relation:

$$\Delta\phi = r\sqrt{\frac{\omega\mu_s'}{6c}}, \quad (1)$$

where c is the speed of light, $\omega$ is the angular frequency of modulation, and $\mu_s'$ is the reduced scattering coefficient. The reduced scattering coefficient for a tissue bed accounts for both blood and surrounding tissue components. This can be written as:

$$\mu_{s\_total}' = V_{blood}\mu_{s\_blood}' + V_{tissue}\mu_{s\_tissue}' \quad (2).$$

The time varying component of equation (1) at a single wavelength will generally be only the portion due to arterial blood. The time varying component of equation (1) at a second wavelength will allow for the deconvolution of the scattering coefficient. The scattering coefficient for blood is related to the hematocrit (HCT) through the following relation:

$$\mu_{s\_blood}' = \sigma_s(1-g)(HCT/V_i)(1-HCT)(1.4-HCT) \quad (3),$$

where g is the anisotropy factor, $\sigma$ is the scattering cross section of an erythrocyte, Vi is the volume of an erythrocyte and HCT is the hematocrit.

As indicated above, the phase of the PDW signals may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using a standard ratio of ratios (e.g., ratrat) technique for the constant and modulated values of the photon density wave amplitudes at two wavelengths. Once the ratio of ratios values is obtained, it may be mapped to the saturation from clinical calibration curves. In general, the amplitude of the resulting photon density waves after passing through the patient tissue 26 may be described as follows:

$$A = \frac{A_0}{4\pi D r_{sd}} \exp\left[-r_{sd}\sqrt{\frac{[(\mu_a c)^2 + \omega^2]^{\frac{1}{2}} + \mu_a c}{2D}}\right], \quad (4)$$

where $A_0$ is the initial amplitude, D is the diffusion coefficient given as $$D = \frac{c}{3(\mu'_s + \mu_a)}, \mu_a$$

is the absorption coefficient, and $r_{sd}$ is the distance between the emitter and the detector.

With regard to phase shift measurements, when the wavelength of the photon density waves is less than a mean absorption distance of the pulsatile tissue 26, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the puddle hematocrit. In general, the change in phase of the resulting photon density waves after passing through the patient tissue 26 may be described as follows:

$$\Delta\Phi = r_{sd}\sqrt{\frac{[(\mu_a c)^2 + \omega^2]^{\frac{1}{2}} - \mu_a c}{D}} + \Phi_0, \quad (5)$$

where $\Phi_0$ is a constant.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, in some embodiments, the driving circuit 28 may perform a frequency sweep over time (e.g., from 100 MHz to 1 GHz) to reduce the error in the determination of a single value of reduced scattering coefficient for the blood and a single value of absorption coefficient.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular $SpO_2$ value should correspond to a particular phase variation at a given frequency. In other words, there may be a certain phase change that should accompany a given increase in absorber that may be observed as a change in amplitude. Various known techniques (e.g., learning based algorithms such as support vector machines, cluster analysis, neural networks, and PCA) based on the measured phase shift and amplitude change may be compared to determine if the amplitude shift and phase shift correlate to a known $SpO_2$. If both the measured amplitude shift and phase shift correlate to a known $SpO_2$, the measured $SpO_2$ value may be deemed appropriate and displayed or utilized as a correct $SpO_2$ value. Alternatively, if the measured amplitude shift and phase shift do not agree, the calculated $SpO_2$ value may be identified as being corrupt or including too much noise and, thus, may be discarded.

As shown in FIG. 2, the patient monitor 12 may include the general- or special-purpose microprocessor 48 on the bus 49, which may govern other general operations of the patient monitor 12, such as how data from the DSP 46 is employed by other components on the bus 49. A network interface card (NIC) 50 may enable the patient monitor 12 to communicate with external devices on a network. A read only memory (ROM) 52 may store certain algorithms, such as those used by the DSP 46 to determine absorption and scattering properties of the patient tissue 26, and nonvolatile storage 54 may store longer long-term data. Additionally or alternatively the nonvolatile storage 54 may also store the algorithms for determining tissue properties.

Other components of the patient monitor 12 may include random access memory (RAM) 56, a display interface 58, and control inputs 60. The RAM 56 may provide temporary storage of variables and other data employed while carrying out certain techniques described herein. The display interface 58 may allow physiological parameters obtained by the patient monitor 12 to appear on the display 20. The control inputs 60 may enable a physician or other medical practitioner to vary the operation of the patient monitor 12. By way of example, a practitioner may select whether the patient is an adult or neonate, and/or whether the patient tissue 26 is high perfusion or low perfusion tissue. Such a selection with the control inputs 60 may vary the modulation frequency of one or more of the single-wavelength PDW signals, may disable one or more of the single-wavelength PDW signals, or may cause a preprogrammed sequence of operation, such as a sweep of modulation frequencies for one or more of the single-wavelength PDW signals, to begin.

Figure 3:
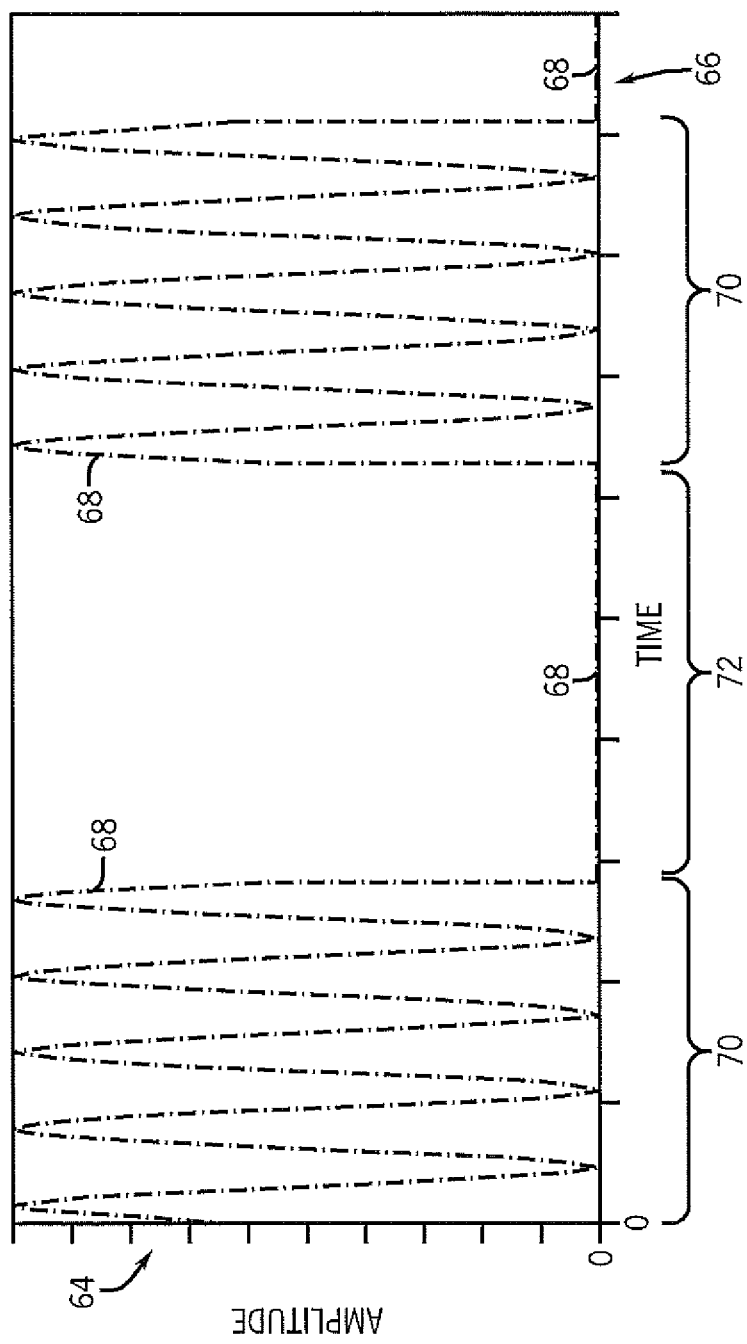
FIG. 3 is a plot of a first single-wavelength photon density wave signal for use in the system of FIG. 1, in accordance with an embodiment.

As noted above, the driving circuit 28 may emit several single-wavelength PDW signals that may be selected by the optical switch 36 to generate one multi-wavelength PDW signal which is sent to the sensor 14. FIG. 3 includes a plot 62 representative of one single-wavelength PDW signal of a multi-wavelength PDW signal. As the multi-wavelength PDW signal includes more than one single-wavelength PDW signal alternating in time, the single-wavelength PDW signal illustrated in the plot 62 may be referred to as the first PDW signal 68 in order to distinguish it from subsequent single-wavelength PDW signals which may alternate with the first PDW signal 68 in a multi-wavelength PDW signal. In the plot 62, the amplitude 64 of the first PDW signal 68 (e.g., a 660 nm PDW signal) is plotted with respect to time 66. The first PDW signal 68 may be generated by the driving circuit 28 by modulation of one of the light sources 30. It should be understood that in other embodiments, the first single-wavelength component 68 may have a different amplitude, modulation frequency, and/or phase.

The first PDW signal 68 may be active at regular intervals for a given period of time (e.g., approximately several milliseconds) in the time-multiplexed multi-wavelength PDW signal. An active interval 70 of the first PDW signal 68 may correspond with a time period during which the optical switch 36 selects a first single-wavelength PDW signal (e.g., via a first optical cable 32) from one of the light sources 30 in the driving circuit 28, such that the first PDW signal 68 is transmitted to the emitter output 22 in the sensor 14 to be emitted into the patient tissue 26. An inactive interval 72 of the first single-wavelength PDW signal 68 may correspond with a time period where the optical switch 36 does not select the first single-wavelength PDW signal, and instead selects a single-wavelength PDW signal modulated from another one of the light sources 30 (e.g., via a second optical cable 34).

As noted below with reference to FIGS. 4 and 5, the first PDW signal 68 may be combined with other single-wavelength PDW signals into a multi-wavelength PDW signal. The optical switch 36 may thus select the first PDW signal 68 at intervals and for periods of time related to the number of other emitted single-wavelength PDW signals to be combined into the multi-wavelength PDW signal. For example, if the first PDW signal 68 is one of two single-wavelength PDW signals emitted by the driving circuit 28, the first PDW signal 68 may be selected by the optical switch 36 for approximately half of the time, as shown in the plot 62. In some embodiments, optical switch 36 may also select different single-wavelength PDW signals to be combined into the multi-wavelength PDW signal at disproportionate amounts of time. For example, disproportionate emissions may be random, or may be affected by factors such as efficiency of the driving circuit 28, the detector 42, and/or the optical switch 36 in emitting and receiving a signal of a certain wavelength, or by the scattering or absorption coefficients of certain patient tissue 26 components.

Figure 4:
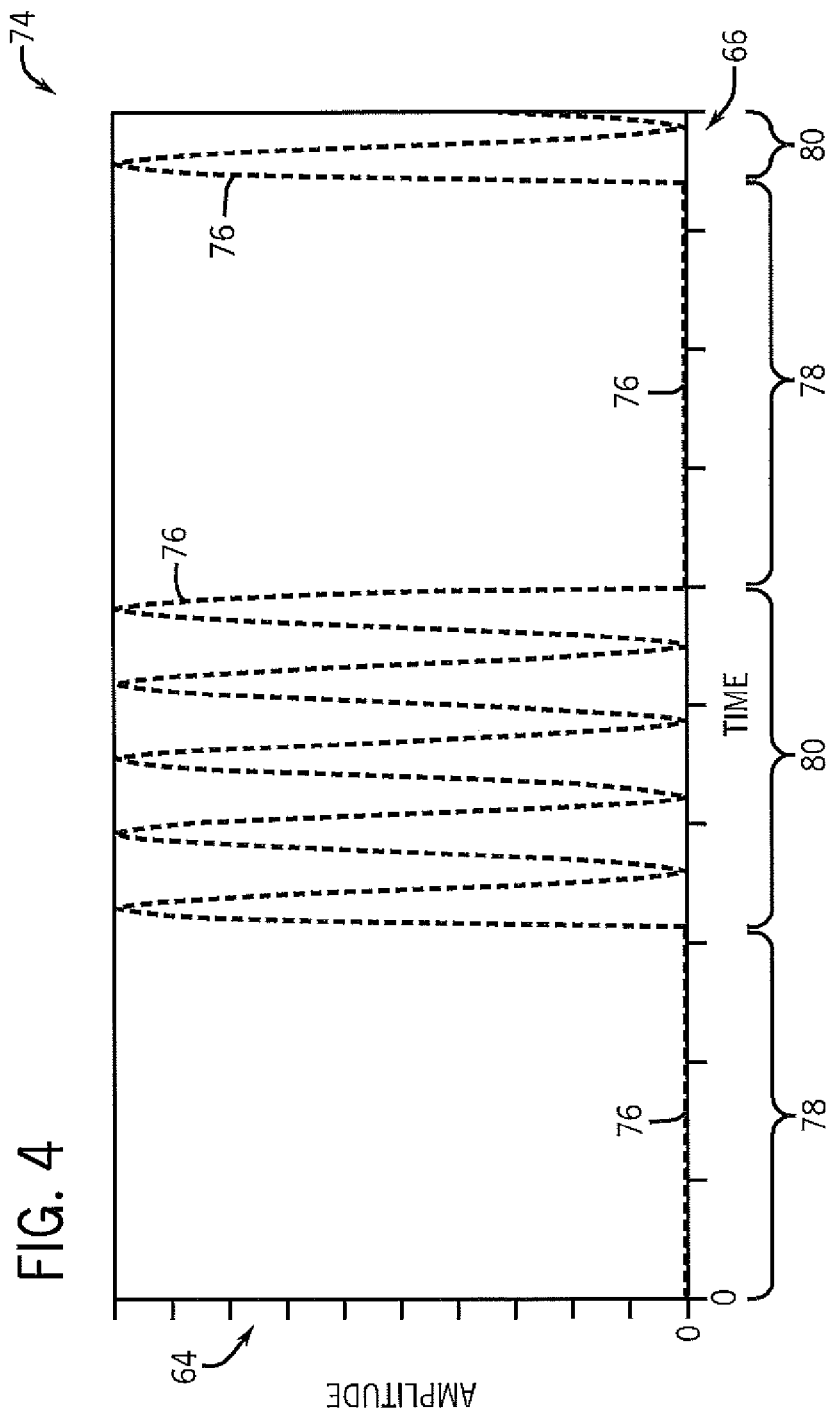
FIG. 4 is a plot of a second single-wavelength photon density wave signal for use in the system of FIG. 1, in accordance with an embodiment.
Figure 5:
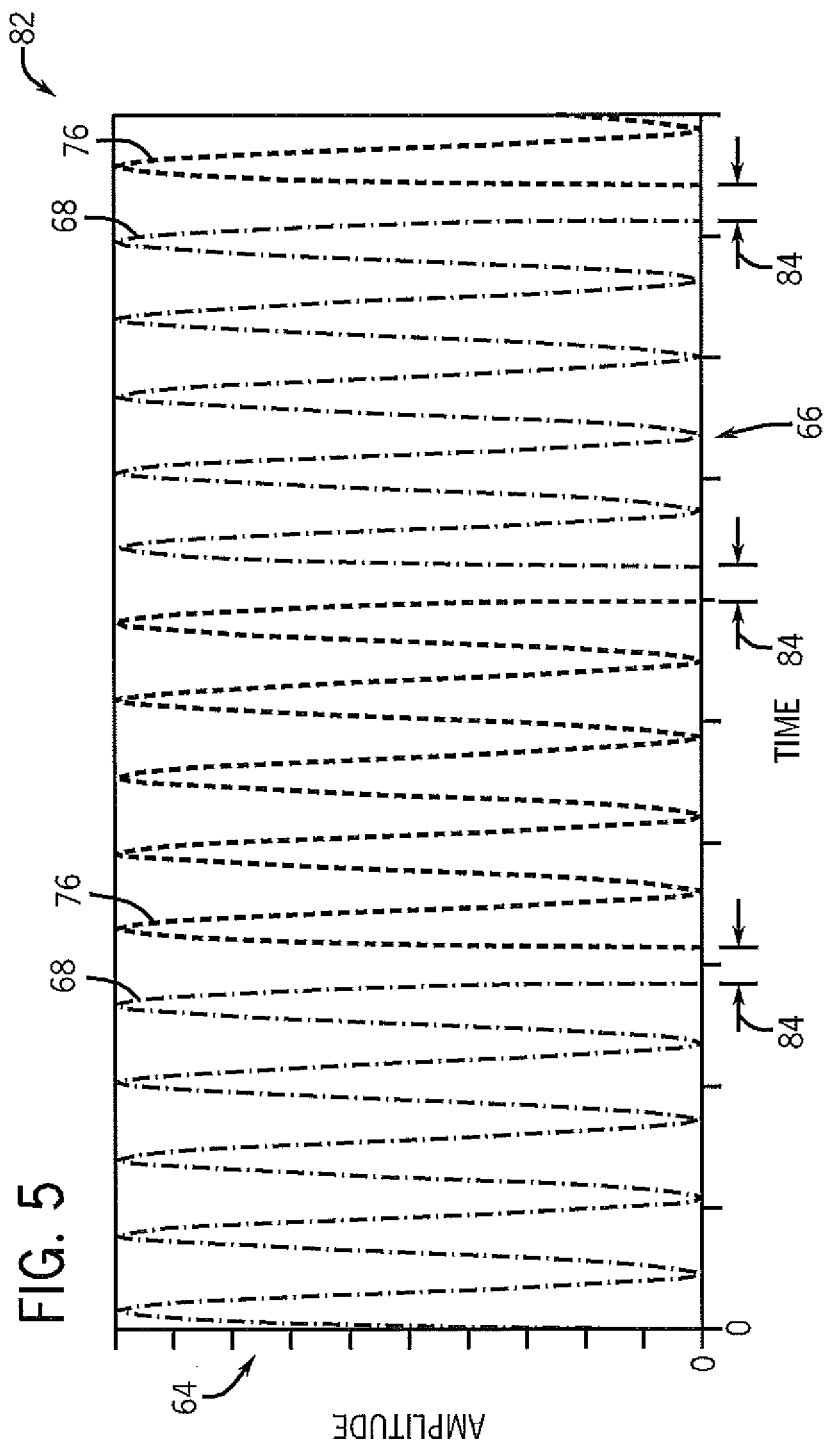
FIG. 5 is a plot of a multi-wavelength photon density wave signal combining the first and second single-wavelength photon density wave signals of FIGS. 3 and 4, in accordance with an embodiment.

FIG. 4 is a plot 74 that represents another single-wavelength PDW signal from a multi-wavelength PDW signal in accordance with present embodiments. This single-wavelength PDW signal may be referred to as the second PDW signal 76, as it may be the second single-wavelength PDW signal to become active in a multi-wavelength PDW signal. In the plot 74, the amplitude 64 of the second PDW signal 76 (e.g., an 808 Hz PDW signal), is plotted with respect to time 66. The second PDW signal 76 may be generated by the driving circuit 28 by modulation of one of the light sources 30. The second single-wavelength PDW signal 76 may be active at regular intervals for a given period of time (e.g., approximately several milliseconds) for time-division multiplexing with one or more other PDW signals, such as the first PDW signal 68. This active period 80 may correspond an inactive period of the first PDW signal 68 of the plot 62, due to the selective switching of the optical switch 36 (e.g., between optical cables 32 and 34). Similarly, the inactive period 78 of the second PDW signal 76 may correspond to an active period of the first PDW signal 68. It should be understood that the second PDW signal 76 may alternatively have a different amplitude, modulation frequency, and/or phase.

The first and second PDW signals 68 and 76 emitted by the driving circuitry 28 may be selected by the optical switch 36 and combined as a single multi-wavelength PDW signal transmitted through a single emitting optical cable 38 to the sensor 14. FIG. 5 is a plot 82 illustrating such a multi-wavelength PDW signal having single-wavelength PDW signals 68 and 76 time-multiplexed by the optical switch 36 such that the first and second PDW signals 68 and 76 are transmitted in series. In the plot 82, the amplitude 64 of the multi-wavelength PDW signal is plotted with respect to time 66. Because the optical switch 36 may select one single-wavelength PDW signal at one time (e.g., optical cable 32 or optical cable 34), the first and second PDW signals 68 and 76 may occur at different, non-overlapping, times in the multi-wavelength PDW signal of the plot 82. Time division information and/or clock signals related to the plot 82 may be sent to the phase detection circuitry 44 and the DSP 46 such that the two single-wavelength PDW signals 68 and 76 may be later separated into distinct single-wavelength PDW signals. Although not necessary, in some embodiments, a brief dark period 84 (e.g., 3 ns) may separate the first and second PDW signals 68 and 76.

When the multi-wavelength PDW signal of the plot 82 has passed through the pulsatile patient tissue 26, single-wavelength components of the output signal (i.e., portions of the signals 68 and 76 which have propagated through the patient tissue 26) may be isolated (i.e., demultiplexed) in the phase detection circuitry 44 and the DSP 46 using time-division information from the driving circuit 28. Comparing one of the de-multiplexed output signals with the corresponding first or second PDW signals 68 or 76 of the plot 82 may indicate various properties of the patient tissue 26.

Figure 6:
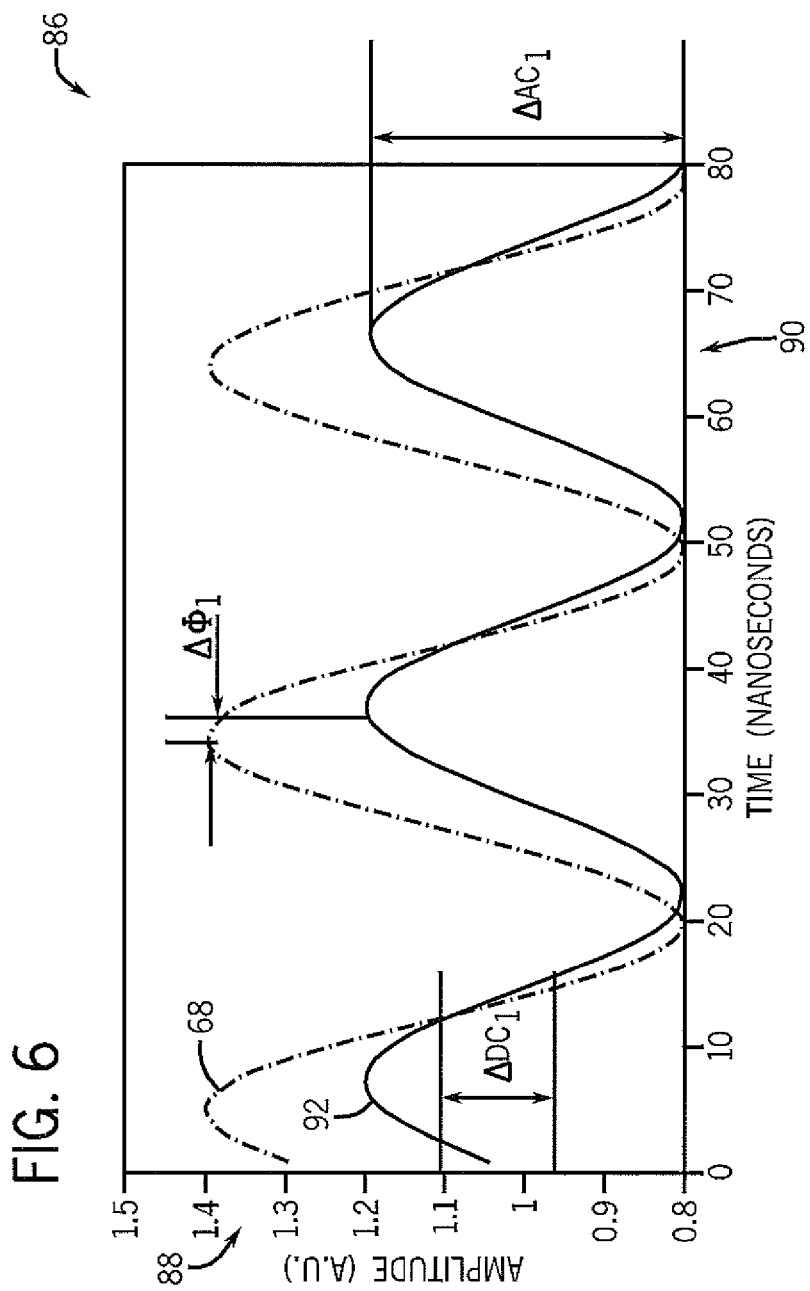
FIG. 6 is a plot representing a comparison between a portion of the multi-wavelength photon density wave signal of FIG. 5 and a received single-wavelength photon density wave signal after the signal of FIG. 5 has been passed through a patient, in accordance with an embodiment.

For example, FIG. 6 illustrates the superimposition of an emitted single-wavelength PDW signal (referred to here as the input signal 68) which may be part of a multi-wavelength PDW signal, with the corresponding detected single-wavelength PDW signal (referred to as the output signal 92). Like the plots 62, 74, and 82 of FIGS. 3-5, plot 86 of FIG. 6 plots a relative amplitude 88 of the input signal 68 and output signal 92 with respect to time 90 in units of nanoseconds (ns). The input signal 68 and the corresponding output signal 92 may have a DC amplitude difference of $\Delta DC_1$, an AC amplitude difference of $\Delta AC_1$, and a phase difference of $\Delta\phi_1$. The amplitude measurements $\Delta DC_1$ and $\Delta AC_1$ may correspond essentially only to absorption in the patient tissue 26, while the phase difference $\Delta\phi_1$ may correspond essentially only to scattering in the patient tissue 26, as generally described with reference to FIG. 8 below.

Since another single-wavelength PDW signal, such as the second PDW signal 76, may occur very shortly thereafter, performing a similar comparison with the following single-wavelength PDW signal may yield additional measurements for absorption and scattering properties of the patient tissue 26 for the second wavelength, at substantially the same time. Thus, the patient monitor 12 may determine at least four measurements associated with properties of the patient tissue 26 for substantially the same time for medical purposes associated with pulse oximetry, including two absorption and two scattering properties. In other words, because substantially no perceptible change in the pulsatile tissue of the patient may occur between the start of the first PDW signal 68 and the start of the second PDW signal 76, for purposes of pulse oximetry, the four measurements may be understood to occur at substantially the same time. Furthermore, the emissions of the first PDW signal 68 and the second PDW signal 76 may be sufficiently frequent to adequately sample pulse from the patient tissue 26 using, for example, the patient monitor 12 (from FIGS. 1 and 2).

Figure 7:
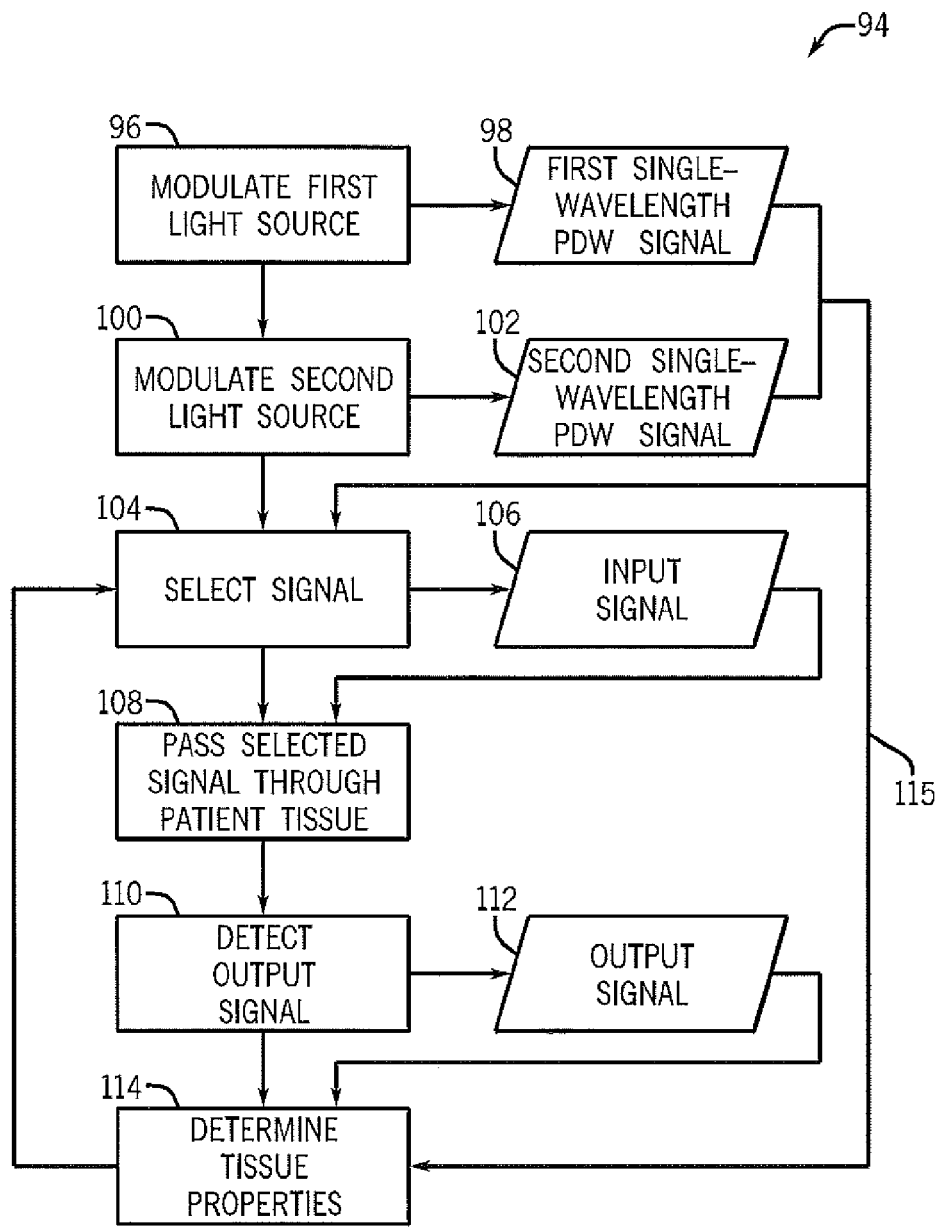
FIG. 7 is a flowchart representing an embodiment of a method for obtaining physiological measurements using the system of FIG. 1, in accordance with an embodiment.

FIG. 7 illustrates a flowchart 94, which represents an embodiment of a method for performing a multi-wavelength PDW measurement using an optical switch. In a first step 96, the driving circuit 28 may modulate a light source (one of the light sources 30) emitting a first wavelength (e.g., a 660 nm wavelength) at a modulation frequency sufficient to produce resolvable photon density waves within the patient tissue 26 to produce a first single-wavelength PDW signal 98. The modulation frequency may result in a PDW wavelength shorter than a mean absorption distance of the pulsatile tissue 26. In other words, such modulation frequency may exceed the product of the mean absorption coefficient multiplied by the speed of light. Thus, depending on the patient tissue 26, the modulation frequency may be between 50 MHz to 3 GHz. In some embodiments, the light source may be modulated at a frequency of approximately 500 MHz. Similarly, in step 100, the driving circuit 28 may also modulate another light source (another of the light sources 30) emitting a second wavelength in substantially the same manner as in step 96 to produce a second single-wavelength PDW signal 102. While only two single-wavelength PDW signals (e.g., 98 and 102) are depicted, in accordance with the present techniques, a plurality of single-wavelength PDW signals may be produced and time-multiplexed to form a multi-wavelength PDW signal.

In step 104, the optical switch 36 may select the first PDW signal 98 or the second PDW signal 102 for transmission via the single optical cable 38 to be emitted into the patient tissue 26. The selected single-wavelength PDW signal, referred to as the input signal 106, may pass through the patient tissue 26 in step 108 (e.g., emitted from the emitter output 22 of the sensor 14). Once the input signal 106 has propagated through the patient tissue 26, portions of the input signal 106 (including light that has been scattered by, reflected by, or transmitted through the tissue) may be received at a detector input 24 of the sensor 14 and passed through a receiving optical cable 40 to the detector 42, as represented by step 110. In step 114, such portions of the detected signal, also referred to as the output signal 112, may be used by the DSP 46 and/or the microprocessor 48 to determine properties of the patient tissue 26 based on phase and amplitude changes between the output signal 112 and the input signal 106 which correspond to scattering and absorption properties in the tissue.

Portions of the process 94, including steps 104, 108, 110, and 114, may repeat indefinitely to generate and emit a multi-wavelength PDW signal into the patient tissue 26 tissue. More specifically, in each iteration of steps 104, 108, 110, and 114, the selected input signal 106 may represent a single-wavelength PDW signal of a multi-wavelength PDW signal, and by alternately selecting a different input signal 106 (e.g., alternating between the first signal 98 and the second signal 102), a multi-wavelength PDW signal may be emitted and detected. In some embodiments, the repetition may be between steps 104, 108, and 110, and the determination and/or analyses of phase and amplitude changes may occur after multiple repetitions of steps 104, 108, and 110, and after a certain length of a multi-wavelength PDW signal has been emitted and detected from the patient tissue 26. Furthermore, the line 115 drawn from the first and second signals 98 and 102 to step 114 may represent that information, such as time-division information, clock signals, and/or reference signals relating to the corresponding original emitted single-wavelength PDW signals 98 and 102 may be used in step 114.

Figure 8:
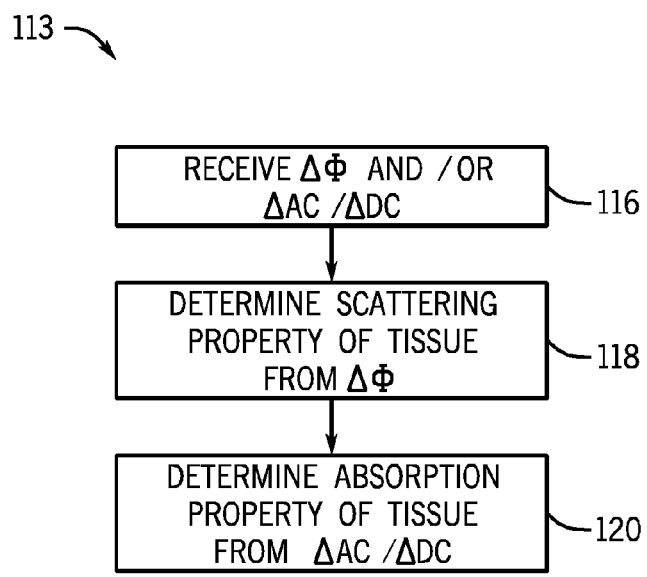
FIG. 8 is a flowchart representing an embodiment of an algorithm for use by the system of FIG. 1 for determining scattering and absorption properties of patient tissue.

FIG. 8 is a flowchart 113, which represents an algorithm that may be used by a processor, such as the DSP 46 of the patient monitor 12, to determine physiological properties of the patient tissue 26 using values obtained by passing a multi-wavelength PDW signal through the patient tissue 26. It should be understood that the flowchart 113 is essentially a more detailed illustration of step 114 of FIG. 7. In a first step 116 of the flowchart 113, phase change $\Delta\phi_1$ and/or amplitude change $\Delta DC_1$ and/or $\Delta AC_1$ values of an output signal 112 may be received into or determined by a processor, such as the DSP 46. Such phase or amplitude changes may be determined based on a comparison between the output signal 112 and a reference signal of a corresponding input signal 106. In step 118, the DSP 46 may determine a scattering property of the patient tissue 26 for the moment in time at which the single-wavelength PDW component of the multi-wavelength PDW signal has passed through the pulsatile tissue 26. Generally, the scattering property may be represented by a scattering coefficient, and may be determined based on the phase change $\Delta\phi_1$ value obtained in step 116 by using Equation (1).

In step 120, the DSP 46 may determine an absorption property of the patient tissue 26 for the moment in time at which the single-wavelength component of the multi-wavelength PDW signal has passed through the pulsatile tissue 26. Generally, the absorption property may be represented by an absorption coefficient, and may be determined based on the amplitude change $\Delta DC_1$ and/or $\Delta AC_1$ values obtained in step 116 by using Equations (1) and (4).

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A system comprising:
   a patient monitor configured to:
     generate a plurality of single-wavelength photon density wave ("PDW") input signals by modulating a plurality of light sources at one or more modulation frequencies sufficient to produce resolvable photon density waves in pulsatile tissue of a patient;
     alternately select one of the plurality of single-wavelength PDW input signals for transmission in series to generate a multi-wavelength PDW input signal;
     receive a multi-wavelength PDW output signal resulting after the multi-wavelength PDW input signal is passed through the pulsatile tissue; and
     determine a scattering property or an absorption property of the pulsatile tissue based at least in part on a comparison between the multi-wavelength PDW output signal and the multi-wavelength PDW input signal; and
   a sensor having an emitter output and a detector input, wherein the emitter output is configured to pass the multi-wavelength PDW input signal into the pulsatile tissue and wherein the detector input is configured to receive the multi-wavelength PDW output signal from the pulsatile tissue of the patient; and
   a sensor cable coupled to the sensor and having a first optical cable configured to transmit the multi-wavelength PDW input signal from the patient monitor to the sensor and having a second optical cable configured to transmit the multi-wavelength PDW output signal from the sensor to the patient monitor, wherein the sensor cable comprises no more than two optical cables.

2. The system of claim 1, wherein the plurality of light sources comprise two or more of a red light source, an infrared light source, and a near infrared light source.

3. The system of claim 1, wherein the plurality of light sources are configured to simultaneously emit light.

4. The system of claim 1, wherein the patient monitor comprises an optical switch configured to alternately select one of the plurality of single-wavelength PDW input signals to generate the multi-wavelength PDW input signal.

5. The system of claim 1, wherein the patient monitor comprises an optical switch configured to time-division multiplex the plurality of single-wavelength PDW input signals.

6. The system of claim 1, wherein the patient monitor is configured to determine a physiological parameter of the patient based at least in part on a comparison of the multi-wavelength PDW output signal and the multi-wavelength PDW input signal.

7. The system of claim 1, wherein the patient monitor is configured to demultiplex the multi-wavelength PDW output signal into a plurality of single-wavelength PDW output signals, wherein each of the plurality of single-wavelength PDW output signals correspond to each of the plurality of single-wavelength PDW input signals.

8. The system of claim 7, wherein the patient monitor is configured to determine a physiological parameter of the patient based at least in part on a change in phase between one of the plurality of single-wavelength PDW output signals and a corresponding one of the plurality of single-wavelength PDW input signals.

9. The system of claim 7, wherein the patient monitor is configured to determine a physiological parameter of the patient based at least in part on a change in amplitude between one of the plurality of single-wavelength PDW output signals and a corresponding one of the plurality of single-wavelength PDW input signals.

10. A patient monitor comprising:
a plurality of light sources configured to simultaneously emit a plurality of wavelengths of light;
a driving circuit configured to modulate the plurality of light sources at one or more modulation frequencies sufficient to produce resolvable photon density waves in pulsatile tissue of a patient to produce a plurality of single-wavelength photon density wave ("PDW") input signals; and
an optical switch configured to select one of the plurality of single-wavelength PDW input signals at a time at non-overlapping intervals to generate a multi-wavelength PDW input signal.

11. The patient monitor of claim 10, comprising:
a first optical cable connector configured to provide the multi-wavelength PDW input signal to a first optical cable of a medical sensor configured to be attached to the pulsatile tissue; and
a second optical cable connector configured to receive a multi-wavelength PDW output signal from a second optical cable of the medical sensor, wherein the multi-wavelength PDW output signal results from propagating the multi-wavelength PDW input signal through the pulsatile tissue.

12. The patient monitor of claim 10, comprising data processing circuitry configured to process the multi-wavelength PDW output signal into a plurality of single-wavelength PDW output signals and configured to determine a physiological parameter of the patient based at least in part on a comparison of one of the plurality of single-wavelength PDW output signals to a corresponding one of the plurality of single-wavelength PDW input signals.

13. The patient monitor of claim 10, wherein the plurality of light sources comprise a plurality of laser diodes.

14. The patient monitor of claim 10, wherein the driving circuit is configured to modulate the plurality of light sources such that each of the plurality of single-wavelength PDW input signals has a different respective modulation frequency.

15. The patient monitor of claim 10, wherein the optical switch is configured to select one of the plurality of single-wavelength PDW input signals by mechanically switching between the plurality of single-wavelength PDW input signals.

16. The patient monitor of claim 10, wherein the data processing circuitry is configured to:
determine an absorption property of the pulsatile tissue based at least in part on a change in amplitude between the one of the plurality of single-wavelength PDW output signals and the corresponding one of the plurality of single-wavelength PDW input signals; and
determine a scattering property of the pulsatile tissue based at least in part on a change in phase between the one of the plurality of single-wavelength PDW output signals and the corresponding one of the plurality of single-wavelength PDW input signals.

17. A method comprising:
simultaneously emitting light from a first light source having a first wavelength and from a second light source having a second wavelength;
generating a first photon density wave ("PDW") signal by modulating the first light source using a driving circuit;
generating a second PDW signal by modulating the second light source using the driving circuit;
selecting and transmitting through tissue the first PDW input signal for a first period of time;
selecting and transmitting through the tissue the second PDW input signal for a second period of time, wherein the first period of time and the second period of time do not overlap;
receiving as a first PDW output signal the first PDW input signal after propagating through the tissue;
receiving as a second PDW output signal the second PDW input signal after propagating through the tissue; and
comparing the first and second PDW output signals to the respective first and second PDW input signals to determine physiological information using phase detection circuitry, signal processing circuitry, or data processing circuitry.

* * * * *